United States Patent
Eller et al.

(10) Patent No.: US 10,016,293 B2
(45) Date of Patent: Jul. 10, 2018

(54) PROSTHESIS DELIVERY SYSTEMS HAVING AN ATRAUMATIC TIP FOR USE WITH TRIGGER WIRES

(71) Applicant: COOK MEDICAL TECHNOLOGIES LLC, Bloomington, IN (US)

(72) Inventors: Derek R. Eller, Bloomington, IN (US); Saylan Lukas, Cincinnati, OH (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 162 days.

(21) Appl. No.: 14/977,041

(22) Filed: Dec. 21, 2015

(65) Prior Publication Data
US 2016/0184122 A1 Jun. 30, 2016

Related U.S. Application Data

(60) Provisional application No. 62/097,479, filed on Dec. 29, 2014.

(51) Int. Cl.
*A61F 11/00* (2006.01)
*A61F 2/966* (2013.01)
*A61F 2/95* (2013.01)

(52) U.S. Cl.
CPC .............. *A61F 2/966* (2013.01); *A61F 2/95* (2013.01); *A61F 2002/9511* (2013.01)

(58) Field of Classification Search
CPC .. A61F 2/95; A61F 2/966; A61F 2/962; A61F 2/243; A61F 2/2436; A61F 2/2439; A61F 2002/9505; A61F 2002/9511; A61F 2002/9517; A61F 2002/9528; A61F 2002/9534

USPC ................ 606/108; 623/1.11, 2.11
See application file for complete search history.

(56) References Cited

U.S. PATENT DOCUMENTS

| 7,147,657 | B2 | 12/2006 | Chiang et al. |
| 7,435,253 | B1 | 10/2008 | Hartley et al. |
| 7,553,323 | B1 | 6/2009 | Perez et al. |
| 2006/0004433 | A1* | 1/2006 | Greenberg ................ A61F 2/07 623/1.11 |

(Continued)

FOREIGN PATENT DOCUMENTS

| EP | 2604232 | 6/2013 |
| WO | WO96/18361 | 6/1996 |

OTHER PUBLICATIONS

Extended European Search Report for EP15275272 dated Jun. 3, 2016, 7 pgs.
Office Action dated Aug. 8, 2017 for EP15275272.1, 4 pgs.

*Primary Examiner* — Melanie Tyson
(74) *Attorney, Agent, or Firm* — Brinks Gilson & Lione

(57) ABSTRACT

The present embodiments provide delivery systems. In one embodiment, the delivery system includes a cannula having proximal and distal regions and a lumen extending therebetween. An atraumatic tip is coupled to the proximal region of the cannula. A proximal region of a housing component is disposed at least partially within a cavity of the atraumatic tip and secured to the atraumatic tip, and a distal region of the housing component extends at least partially distally beyond the atraumatic tip. A proximal region of a trigger wire is housed within the distal region of the housing component in a delivery state.

17 Claims, 3 Drawing Sheets

(56) References Cited

U.S. PATENT DOCUMENTS

| | | |
|---|---|---|
| 2008/0140178 A1 | 6/2008 | Rasmussen et al. |
| 2010/0234932 A1 | 9/2010 | Arbefeuille et al. |
| 2012/0109280 A1 | 5/2012 | McHugo |
| 2012/0239130 A1 | 9/2012 | Hartley et al. |
| 2013/0131775 A1* | 5/2013 | Hadley .................. A61F 2/966 623/1.11 |
| 2013/0297011 A1* | 11/2013 | Morris ................. A61F 2/2436 623/2.11 |
| 2014/0121749 A1 | 5/2014 | Roeder |

* cited by examiner

PROSTHESIS DELIVERY SYSTEMS HAVING AN ATRAUMATIC TIP FOR USE WITH TRIGGER WIRES

PRIORITY CLAIM

This invention claims the benefit of priority of U.S. Provisional Application Ser. No. 62/097,479, entitled "Prosthesis Delivery Systems Having an Atraumatic Tip for Use with Trigger Wires," filed Dec. 29, 2014, the disclosure of which is hereby incorporated by reference in its entirety.

BACKGROUND

The present embodiments relate generally to medical devices, and more particularly, to apparatus and methods for deployment of prostheses.

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter reducing ties. With self-expanding stents, the stents expand primarily based on their own expansive force without the need for further mechanical expansion. In a stent made of a shape-memory alloy such as nitinol, the shape-memory alloy may be employed to cause the stent to return to a predetermined configuration upon removal of the sheath or other device maintaining the stent in its predeployment configuration.

When trigger wires are used as a deployment control mechanism, the trigger wires may releasably couple the proximal and/or distal ends of a stent or stent-graft to a delivery catheter. Typically, one or more trigger wires are looped through a portion of the stent near a vertex of the stent. For example, trigger wires may be used to restrain a "Z-stent" or Gianturco stent comprising a series of substantially straight segments interconnected by a series of bent segments. The trigger wires may be disposed through, and pull upon, the bent segments to pull the stent closely against the delivery catheter. Trigger wires also may be used in conjunction with different stent designs, such as cannula-cut stents having acute or pointed bends.

If trigger wires are used to deploy stents, proximal ends of the trigger wires may be disposed beneath an atraumatic tip of the delivery system. The atraumatic tip may require a relatively long length in order to house a significant length of the trigger wires therein. However, atraumatic tips of relatively long lengths may not be desirable in certain delivery situations, including but not limited to when needing to deploy a stent in the ascending aorta without disrupting the aortic valve.

SUMMARY

The present embodiments provide delivery systems. In one embodiment, the delivery system comprises a cannula having proximal and distal regions and a lumen extending therebetween. An atraumatic tip is coupled to the proximal region of the cannula. A proximal region of a housing component is disposed at least partially within a cavity of the atraumatic tip and secured to the atraumatic tip, and a distal region of the housing component extends at least partially distally beyond the atraumatic tip. A proximal region of a trigger wire is housed within the distal region of the housing component in a delivery state.

In one example, the distal region of the housing component comprises at least one channel, and the trigger wire is housed within the channel of the housing component in the delivery state. In another example, the distal region of the housing component comprises an annular cavity in a space between the cannula and the housing component, and the trigger wire is housed within the cavity of the housing component in the delivery state.

In some examples, a sleeve having proximal and distal regions is provided. A portion of the proximal region of the sleeve may be disposed coaxially between the atraumatic tip and the housing component. The distal region of the trigger wire may be disposed coaxially between the cannula and the distal region of the sleeve in the delivery state. Inner and outer diameters at the proximal region of the sleeve may be greater than inner and outer diameters at the distal region of the sleeve. Two openings may be formed in the sleeve, and the trigger wire forms a loop external to the sleeve between the two openings in the delivery state.

In one embodiment, the proximal region of the housing component is secured to the atraumatic tip using a threaded engagement. Further, a proximal end of the cannula may be flared radially outward within the cavity of the atraumatic tip at a location distal to the housing component.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

Figure 1:
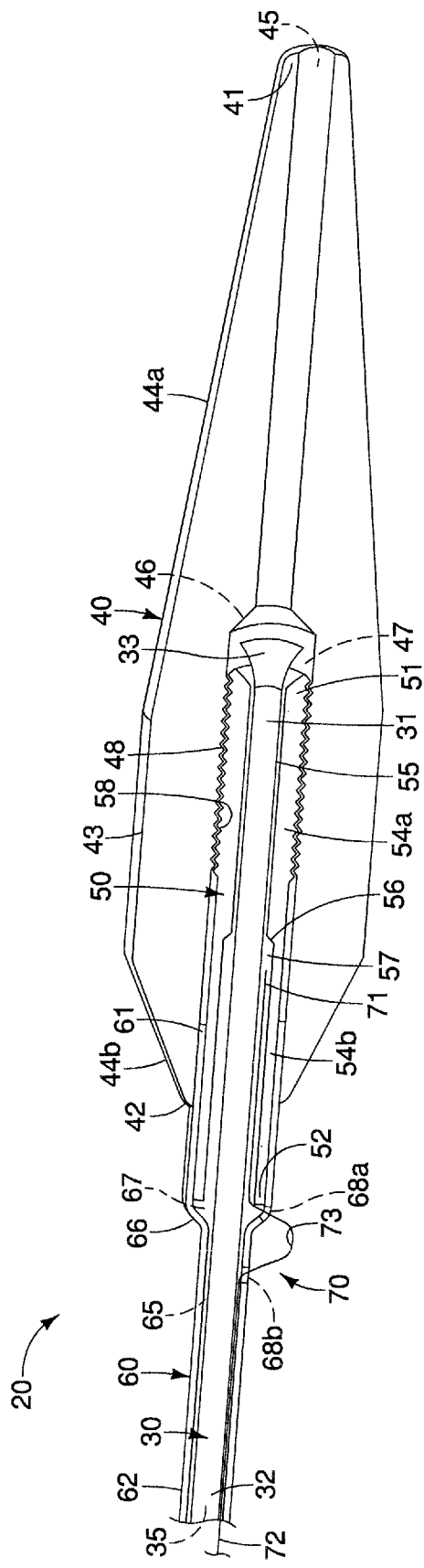
FIG. 1 is a side-sectional view of a first embodiment of a prosthesis delivery system.

Referring to FIG. 1, a first embodiment of a prosthesis delivery system 20 is shown. The system 20 comprises a cannula 30, an atraumatic tip 40, a housing component 50, a sleeve 60, and at least one trigger wire 70, each of which are described in further detail below.

The cannula 30 comprises a tubular member having proximal and distal regions 31 and 32, and a lumen 35 extending between the proximal and distal regions 31 and 32. The lumen 35 of the cannula 30 is sized to allow the cannula 30 to be advanced over a wire guide.

The atraumatic tip 40 may be formed from an atraumatic material, which comprises proximal and distal ends 41 and 42, respectively, with an intermediate region 43 disposed therebetween. A proximal taper 44a increases the outer diameter of the atraumatic tip in a direction from the proximal end 41 to the intermediate region 43, while a distal taper 44b decreases the outer diameter of the atraumatic tip in a direction from the intermediate region 43 to the distal end 42, as depicted in FIG. 1. The intermediate region 43, positioned between the proximal and distal tapers 44a and 44b, may comprise an axially-extending region of substantially uniform outer diameter as depicted in FIG. 1, or alternatively may comprise a single point that does not extend a substantial axial distance.

The atraumatic tip 40 further comprises a lumen 45, a cavity 47, and a taper 46 disposed between the lumen 45 and the cavity 47, as shown in FIG. 1. The lumen 45 extends proximally from the taper 46 to the proximal end 41 of the atraumatic tip 40, while the cavity 47 extends distally from the taper 46 to the distal end 42 of the atraumatic tip 40, as shown in FIG.

An inner diameter of the cavity 47 is greater than an inner diameter of the lumen 45. The lumen 45 may comprise an inner diameter that is approximately equal to, or slightly greater than, an outer diameter of the cannula 30. While the cannula 30 is depicted as terminating distal to the lumen 45 of the atraumatic tip 40 in the embodiment of FIG. 1 due to the provision of a flared proximal section 33 of the cannula 30, explained further below, in an alternative embodiment the cannula 30 may extend proximally within the lumen 45 of the atraumatic tip 40 and an outer surface of the cannula 30 optionally may engage an inner surface of the lumen 45 using a friction fit.

The housing component 50 comprises proximal and distal ends 51 and 52, and further comprises proximal and distal regions 54a and 54b, respectively. The housing component 50 further comprises a lumen 55, a cavity 57, and a taper 56 disposed between the lumen 55 and the cavity 57, as shown in FIG. 1. The lumen 55 extends within the proximal region 54a in a proximal direction from the taper 56 to the proximal end 51 of the housing component 50, while the cavity 57 extends within the distal region 54b in a distal direction from the taper 56 to the distal end 52 of the housing component 50, as shown in FIG. 1.

An inner diameter of the cavity 57 is greater than an inner diameter of the lumen 55. The lumen 55 may comprise an inner diameter that is approximately equal to, or slightly greater than, an outer diameter of the cannula 30. The proximal region 54a of the housing component 50 may be secured to the cannula 30, for example, using an adhesive, solder, mechanical coupling or other suitable member. In one embodiment, the cannula 30 comprises the flared proximal section 33, which may provide additional support for securement of the proximal region 54a of the housing component 50 to the cannula 30.

The housing component 50 is disposed at least partially within the cavity 47 of the atraumatic tip 40, and further is disposed coaxially between portions of the cannula 30 and the atraumatic tip 40, as shown in FIG. 1. The proximal region 54a of the housing component 50 may be secured to the atraumatic tip 40. In one embodiment, an outer surface of the proximal region 54a of the housing component 50 is secured to an inner surface of the cavity 47 of the atraumatic tip 40. For example, the outer surface of the proximal region 54a may comprise threading 58, which is adapted to mate with threading 48 on the inner surface of the cavity 47. However, alternative engagement mechanisms, including adhesives or mechanical coupling devices, may be used to secure the proximal region 54a of the housing component 50 within the cavity 47 of the atraumatic tip 40.

The sleeve 60 comprises proximal and distal regions 61 and 62, where the proximal region 61 comprises an outer diameter that is greater relative to an outer diameter of the distal region 62. The sleeve 60 further comprises a lumen 65, a cavity 67, and a taper 66 disposed between the lumen 65 and the cavity 67, as shown in FIG. 1. The lumen 65 extends within the distal region 62 in a distal direction from the taper 66 to the distal end of the sleeve 60, while the cavity 67 extends within the proximal region 61 in a proximal direction from the taper 66 to the proximal end of the sleeve 60, as shown in FIG. 1.

An inner diameter of the cavity 67 is greater than an inner diameter of the lumen 65. The lumen 65 may comprise an inner diameter that is slightly greater than an outer diameter of the cannula 30. The lumen 65 forms an annular space between the sleeve 60 and the cannula 30, and the one or more trigger wires 70 pass through the annular space of the lumen 65, as explained further below.

A portion of the proximal region 61 of the sleeve, including the most proximal end, is disposed between an outer surface of the housing component 50 and an inner surface of the atraumatic tip 40, as shown in FIG. 1. It should be noted that the sleeve 60 increases its overall diameter profile a predetermined distance distal to the atraumatic tip 40. In this manner, an overall outer diameter of the system 20 is relatively small along the distal region 62 of the sleeve 60, then due to the taper 66 the overall outer diameter increases along the portion of the proximal region 61 that does not yet overlap with the atraumatic tip 40, and then the overall outer diameter further increases due to the distal taper 44b of the atraumatic tip 40. Accordingly, there are multiple different tapers that progressively change the outer diameter of the system 20 between the relatively narrow distal region 62 of the sleeve 60 and the relatively wide intermediate region 43 of the atraumatic tip 40.

At least a portion of the distal region 54b of the housing component 50 is disposed within the cavity 67 formed within the proximal region 61 of the sleeve 60, as shown in FIG. 1. In this manner, the distal region 54b of the housing component 50 can extend distally beyond the distal end 42 of the atraumatic tip 40, a feature that will be advantageous for housing a relatively long length of the trigger wires 70 within the housing component 50, while allowing for a reduction in the overall length of the atraumatic tip 40, as will be explained further below. The predetermined distance that the distal region 54b of the housing component 50 extends distally beyond the atraumatic tip 40 can be varied to accommodate a desired length of the trigger wires 70, as explained further below.

The trigger wires 70 may extend a relatively long distance within the lumen 65 formed between the cannula 30 and the sleeve 60. A distal region of the trigger wire 70 extends outside of the patient's body, such that a physician may actuate the trigger wire using conventional techniques when it is desirable to release a predetermined region of a prosthesis. A proximal region 71 of the trigger wire 70 is housed within the cavity 57 formed at the distal region 54b of the housing component 50, as shown in FIG. 1.

The sleeve 60 may comprise proximal and distal openings 68a and 68b, respectively, which allow passage of a particular trigger wire 70. Specifically, the trigger wire 70 extends within the lumen 65 of the sleeve 60, then extends through the distal opening 68b in the sleeve 60, then forms a loop 73 external to the sleeve, and then re-enters the sleeve 60 via the proximal opening 68a, which may be positioned at or near the taper 66, and the trigger wire 70 then extends within the distal region 54b of the housing component 50, as shown in FIG. 1. The loop 73 may be disposed through or around one or more parts of a prosthesis, for example, a region of a prosthesis comprising a self-expanding stent, such that the loop 73 restrains that particular region of the prosthesis in a delivery state.

Distal ends of select components extend outside of the patient's body and have not been shown in FIG. 1. For example, it should be noted that the cannula 30 and the trigger wires 70 extend distally outside of a patient's body in a delivery state, and may be manipulated by a physician outside of the body using conventional techniques. The sheath 60 also may extend distally outside of the patient's body, although this is not required if the trigger wires 70 may be adequately constrained at a location distal to where the sheath terminates.

In one exemplary method of use, a guide wire is inserted into a patient's vasculature towards a target site. Then, the atraumatic tip 40 and the cannula 30 are advanced over the guide wire to the target site, together with the related components of the system 20 shown in FIG. 1 and an endoluminal prosthesis. The delivery system preferably is "pre-loaded," such that before the delivery device is introduced into the patient's vasculature, it is pre-assembled with mechanisms that facilitate prosthesis delivery and deployment already arranged thereon.

During delivery, the loop 73 of the trigger wire 70 restrains one or more regions of the endoluminal prosthesis, which is disposed coaxially over sleeve 70 at a location just distal to the atraumatic tip 40. An outer sheath (not shown) may extend proximally to the atraumatic tip 40 and cover the endoluminal prosthesis. The endoluminal prosthesis may comprise one or more self-expanding components, such as a stent made of a shape-memory material stainless steel, or other suitable material, upon which it is inclined to assume a predetermined expanded shape upon withdrawal of the outer sheath.

Upon initial alignment of the endoluminal prosthesis within the body, the outer sheath may be distally retracted to expose the endoluminal prosthesis. At this time, portions of the endoluminal prosthesis may be inclined to self-expand. However, the loops 73 of the one or more trigger wires 70 maintain portions of the prosthesis in a retracted state. Upon final positioning, the one or more trigger wires 70 may be retracted distally a sufficient amount that causes the proximal end of the trigger wires 70 to pass distally beyond the distal opening 68b, thereby removing the loop 73 and allowing expansion of this portion of the prosthesis into engagement with an inner wall of the body passage.

Advantageously, the design of the system 20 allows for the axial length of the atraumatic tip 40 to be reduced, i.e., the distance between the proximal and distal ends 41 and 42, while still obtaining a relatively long axial pathway for housing of the proximal region 71 of the trigger wire 70. The overall arrangement of parts of the system 20, including but not limited to the provision of the distal region 54b of the housing component 50 distal to the atraumatic tip 40, allows for a relatively long axial pathway for housing the proximal region 71 of the trigger wire 70, yet this relatively long axial pathway does not have to be entirely within the axial length of the atraumatic tip 40, allowing for a reduction in length of the atraumatic tip 40.

An exemplary advantage of reducing the axial length of the atraumatic tip 40 between the proximal and distal ends 41 and 42 is that the atraumatic tip 40 may be maneuvered into bodily regions with relatively short landing zones. For example, it may be desirable to endovascularly deploy a stent-graft within the ascending aorta, with a delivery direction from the aortic arch towards the aortic valve. The provision of an atraumatic tip 40 with a reduced axial length permits the introduction of the prosthesis deeper into the ascending aorta with a reduced likelihood of reaching or damaging the aortic valve during placement. Alternatively, if the prosthesis to be delivered comprises a replacement aortic valve, then the atraumatic tip 40 may extend partially into the aortic root, but advantageously may not extend further into the heart, thus reducing the likelihood of damaging nearby anatomy. It will be appreciated that numerous other bodily passageways can benefit from the provision of the reduction in axial length of the atraumatic tip 40.

Another exemplary advantage, by providing a cavity 57 of the distal region 54b of the housing component 50 at a location at least partially distally beyond the atraumatic tip 40, is maintaining a relatively long axial pathway for the proximal region 71 of the trigger wire 70 to increase its housing after re-entering the sheath 60 via the proximal opening 68a, thereby reducing its likelihood of premature deployment. The predetermined distance that the distal region 54b of the housing component 50 extends distally beyond the atraumatic tip 40 can be varied to accommodate a desired securely-housed length of the trigger wires 70.

Various further advantages are achieved by overlapping the housing component 50 and the sleeve 60 in the manner shown in FIG. 1. First, there is a degree of contact between the sleeve 60 and the atraumatic tip 40, which may provide greater structural security for both components. Second, the overlap of the housing component 50 and the sleeve 60 helps guide the trigger wires 70 into the cavity 57 within the housing component 50. Further, the overlap of the housing component 50 and the sleeve 60 helps prevent any adhesive used in securing the proximal region 54a of the housing component 50 to the atraumatic tip 40 from traveling into the cavity 57, which is designated to house the trigger wires 70.

Figure 2:
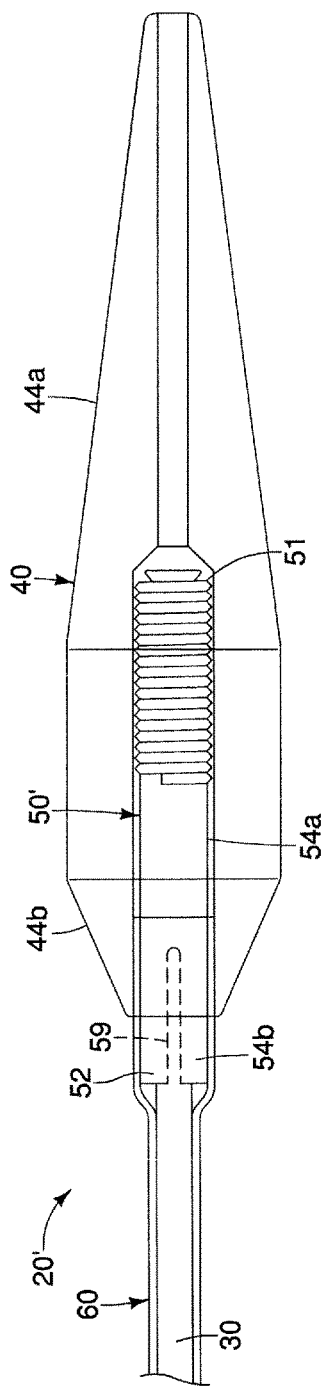
FIGS. 2-3 are a side view and perspective view, respectively, of an alternative embodiment of an prosthesis delivery system, with selected interior components shown with solid lines for illustrative purposes.
Figure 3:
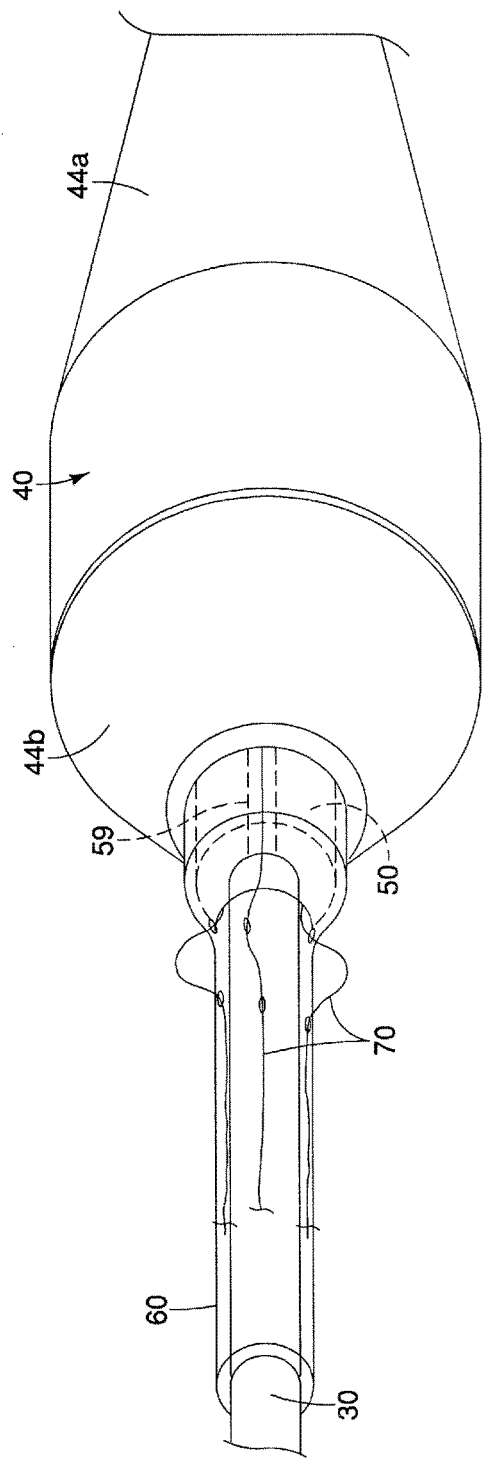

Referring to FIGS. 2-3, an alternative embodiment of a prosthesis delivery system is shown. The alternative delivery system 20' of FIGS. 2-3 is similar to the delivery system 20 of FIG. 1, with a main difference that an alternative housing component 50' is provided. The housing component 50' of FIGS. 2-3 is similar to the housing component 50 of FIG. 1, with a main exception that a plurality of distinct channels 59 are provided extending from the distal end 52, instead of a generally open annular cavity as in the embodiment of FIG. 1. In the embodiment of FIGS. 2-3, a single trigger wire 70 may be disposed within a single channel 59 formed in the housing component 50', such that multiple trigger wires and corresponding channels may be disposed circumferentially around the housing component 50' in spaced-apart relationships. The channels 59 may be formed radially through the entire wall thickness at the distal region 54b of the housing component 50', or alternatively may be etched into inner surfaces along the distal region 54b of the housing component 50'.

Figure 4:
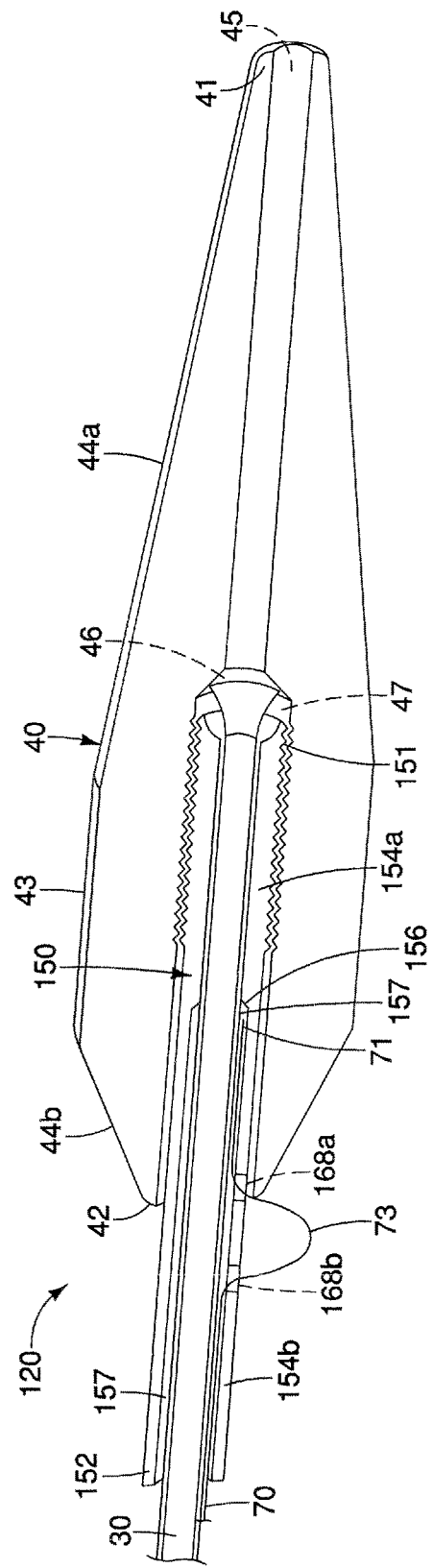
FIG. 4 is a side-sectional view of a further alternative embodiment of a prosthesis delivery system.

Referring to FIG. 4, a further alternative embodiment of a prosthesis delivery system is shown. The alternative delivery system 120 of FIG. 4 is similar to the delivery system 20 of FIG. 1, with a main difference that the sleeve 60 is omitted. In this embodiment, an alternative housing component 150 is provided, and a distal region 154b of the housing component 150 encompasses some of the features and functions as the sleeve 60 previously provided. The housing component 150 comprises proximal and distal ends 151 and 152, proximal and distal regions 154a and 154b, and further comprises a lumen 155, a cavity 157, and a taper 156, in a manner similar to features described with respect to FIG. 1. In the embodiment of FIG. 4, the distal region 154b extends further distally, and comprises proximal and distal openings 168a and 168b, which permit passage of the trigger wires 70 to form loops 73. In this embodiment, since the housing component 150 and the trigger wires 70 each may comprise metal materials, it may be desirable to provide a plastic or elastomeric lining at the proximal and distal openings 168a and 168b to reduce binding. It may be noted that the various exemplary advantages, detailed above with respect to FIG. 1, are still obtained with the alternative embodiments described in FIGS. 2-4.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A delivery system, comprising:
   a cannula having proximal and distal regions and a lumen extending therebetween;
   an atraumatic tip coupled to the proximal region of the cannula;
   a housing component having proximal and distal regions, wherein the proximal region of the housing component is disposed at least partially within a cavity of the atraumatic tip and secured to the atraumatic tip, and wherein the distal region of the housing component extends at least partially distally beyond the atraumatic tip;
   a sleeve having proximal and distal regions, wherein a portion of the proximal region of the sleeve is disposed coaxially between the atraumatic tip and the housing component;
   a trigger wire having proximal and distal regions, wherein the proximal region of the trigger wire is housed within the distal region of the housing component in a delivery state, and wherein the distal region of the trigger wire is disposed coaxially between the cannula and the distal region of the sleeve in the delivery state; and
   a prosthesis, wherein a proximal end of the atraumatic tip is disposed proximal to the prosthesis in the delivery state.

2. The delivery system of claim 1, wherein the distal region of the housing component comprises at least one channel, wherein the trigger wire is housed within the channel of the housing component in the delivery state.

3. The delivery system of claim 1, wherein the distal region of the housing component comprises an annular cavity in a space between the cannula and the housing component, wherein the trigger wire is housed within the cavity of the housing component in the delivery state.

4. The delivery system of claim 3, wherein the proximal region of the housing component comprises a lumen having an inner diameter that approximates an outer diameter of the cannula, wherein an inner diameter of the cavity of the housing component is greater than the inner diameter of the lumen of the housing component.

5. The delivery system of claim 1, wherein inner and outer diameters at the proximal region of the sleeve are greater than inner and outer diameters at the distal region of the sleeve.

6. The delivery system of claim 1, further comprising two openings formed in the sleeve, wherein the trigger wire forms a loop external to the sleeve between the two openings in the delivery state.

7. The delivery system of claim 1, wherein the proximal region of the housing component is secured to the atraumatic tip using a threaded engagement.

8. The delivery system of claim 1, wherein a proximal end of the cannula is flared radially outward within the cavity of the atraumatic tip at a location proximal to the housing component.

9. A delivery system, comprising:
   a cannula having proximal and distal regions and a lumen extending therebetween;
   an atraumatic tip coupled to the proximal region of the cannula;
   a housing component having proximal and distal regions, wherein the proximal region of the housing component is disposed at least partially within a cavity of the atraumatic tip and secured to the atraumatic tip, and wherein the distal region of the housing component extends at least partially distally beyond the atraumatic tip;
   a sleeve having proximal and distal regions, wherein a portion of the proximal region of the sleeve is disposed coaxially between the atraumatic tip and the housing component;
   a trigger wire having proximal and distal regions, wherein the proximal region of the trigger wire is housed within the distal region of the housing component in a delivery state; and
   a prosthesis, wherein a proximal end of the atraumatic tip is disposed proximal to the prosthesis in the delivery state.

10. The delivery system of claim 9, wherein the distal region of the housing component comprises at least one channel, wherein the trigger wire is housed within the channel of the housing component in the delivery state.

11. The delivery system of claim 9, wherein the distal region of the housing component comprises an annular cavity in a space between the cannula and the housing component, wherein the trigger wire is housed within the cavity of the housing component in the delivery state.

12. The delivery system of claim 11, wherein the proximal region of the housing component comprises a lumen having an inner diameter that approximates an outer diameter of the cannula, wherein an inner diameter of the cavity of the housing component is greater than the inner diameter of the lumen of the housing component.

13. The delivery system of claim 9, wherein the distal region of the trigger wire is disposed coaxially between the cannula and the distal region of the sleeve in the delivery state.

14. The delivery system of claim 9, wherein inner and outer diameters at the proximal region of the sleeve are greater than inner and outer diameters at the distal region of the sleeve.

15. The delivery system of claim 9, further comprising two openings formed in the sleeve, wherein the trigger wire formed a loop external to the sleeve between the two openings in the delivery state.

16. The delivery system of claim 9, wherein the proximal region of the housing component is secured to the atraumatic tip using a threaded engagement.

17. The delivery system of claim 9, wherein a proximal end of the cannula is flared radially outward within the cavity of the atraumatic tip at a location proximal to the housing component.

* * * * *